(12) United States Patent
Ravi et al.

(10) Patent No.: US 10,967,199 B2
(45) Date of Patent: Apr. 6, 2021

(54) KNOWLEDGE-BASED BRACHYTHERAPY PLANNING BASED ON PRIMITIVE FEATURES COMPUTED FROM ANATOMICAL CONTOUR DATA

(71) Applicant: Sunnybrook Research Institute, Tononto (CA)

(72) Inventors: Ananth Ravi, Toronto (CA); Alexandru Nicolae, Thornhill (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 318 days.

(21) Appl. No.: 16/077,237

(22) PCT Filed: Feb. 9, 2017

(86) PCT No.: PCT/CA2017/050150
§ 371 (c)(1),
(2) Date: Aug. 10, 2018

(87) PCT Pub. No.: WO2017/136937
PCT Pub. Date: Aug. 17, 2017

(65) Prior Publication Data
US 2019/0030365 A1    Jan. 31, 2019

Related U.S. Application Data

(60) Provisional application No. 62/293,878, filed on Feb. 11, 2016.

(51) Int. Cl.
*A61N 5/10*    (2006.01)
*G16H 50/20*    (2018.01)
(Continued)

(52) U.S. Cl.
CPC .............. *A61N 5/103* (2013.01); *A61B 34/10* (2016.02); *A61N 5/1027* (2013.01); *G16H 10/60* (2018.01);
(Continued)

(58) Field of Classification Search
CPC ........ G16H 50/20; G16H 70/20; G16H 10/60; G16H 20/40; G06F 19/325;
(Continued)

(56) References Cited

U.S. PATENT DOCUMENTS

| 8,199,990 | B2 | 6/2012 | Foshee |
| 8,774,358 | B2 | 7/2014 | Zankowski |

(Continued)

FOREIGN PATENT DOCUMENTS

| WO | 2015168431 A1 | 11/2015 | |
| WO | 2015169498 | 11/2015 | |
| WO | WO-2015169498 A1 * | 11/2015 | ............. A61N 5/103 |

OTHER PUBLICATIONS

Andrea, J. et al. "Measuring radiation treatment plan similarity in the cloud." World Congress on Medical Physics and Biomedical Engineering, Jun. 7-12, 2015, Toronto, Canada. Springer, Cham, 2015.

(Continued)

*Primary Examiner* — Christine H Matthews
*Assistant Examiner* — Joshua Daryl D Lannu
(74) *Attorney, Agent, or Firm* — Quarles & Brady LLP; Jonathan Stone (57) ABSTRACT

Described here are systems and methods for knowledge-based brachytherapy planning. These systems and methods are capable of automatically generating treatment plans for prostate brachytherapy in clinically relevant times. Primitive features computed from anatomical contours of the target organ are used to retrieve a template plan from a database.

(Continued)

The template plan is then adjusted in a stochastic search algorithm.

19 Claims, 7 Drawing Sheets

(51) Int. Cl.
  *G16H 10/60*  (2018.01)
  *A61B 34/10*  (2016.01)
  *G16H 20/40*  (2018.01)
  *G16H 70/20*  (2018.01)

(52) U.S. Cl.
  CPC ............. *G16H 20/40* (2018.01); *G16H 50/20* (2018.01); *G16H 70/20* (2018.01); *A61N 2005/1024* (2013.01); *A61N 2005/1041* (2013.01)

(58) Field of Classification Search
  CPC ... G06F 19/3481; A61B 34/10; A61N 5/1027; A61N 2005/1024; A61N 5/103; A61N 2005/1041
  See application file for complete search history.

(56) References Cited

U.S. PATENT DOCUMENTS

| | | |
|---|---|---|
| 2002/0016695 A1 | 2/2002 | Lee |
| 2012/0197656 A1 | 8/2012 | Lang |
| 2013/0085343 A1 | 4/2013 | Toimela |

OTHER PUBLICATIONS

Cheadle C, et al. 2003. Analysis of microarray data using z score transformation. J Mol Diagn; 5(2): 73-81.

Chng N, et al. 2009. Sci-Fri AM(2): Brachy-09: Using bayesian networks for prostate brachytherapy inverse planning. Med Phys; 36: 4324 [abstract].

Dinkla AM, et al. 2015. A comparison of inverse optimization algorithms for HDR/PDR prostate brachytherapy treatment planning. Brachytherapy; 14(2): 279-88.

Gregory KJ, et al. 2015. Measurement uncertainty analysis of low-dose-rate prostate seed brachytherapy: post-implant dosimetry. Australasian Physical & Engineering Sciences in Medicine; 38(1): 71-81.

Hemanth DJ, et al. Chapter 12: Computational Intelligent Techniques for Pattern Recognition in Biomedical Image Processing Applications. In: Machine Learning Algorithms for Problem Solving in Computational Applications. IGI Global, 2012: 195-7. Doi: 104018/978-4666-1833-6.ch012.

Holmes DR, et al. 2014. Shape analysis of the prostate: establishing imaging specifications for the design of a transurethral imaging device for prostate brachytherapy guidance. Brachytherapy; 13: 465-70.

International Searching Authority, International Search Report and Written Opinion for PCT/CA2017/050150, dated May 23, 2017, 7 pages.

Lahanas M, et al. 2003. A hybrid evolutionary algorithm for multi-objective anatomy-based dose optimization in high-dose-rate brachytherapy. Phys Med Biol; 48(3): 399-415.

Lake BM, et al. 2015. Human-level concept learning through probabilistic program induction. Science; 350(6266): 1332-8.

Lerner AZ. 2004. Inverse planning for low-dose-rate prostate brachytherapy by simulated annealing under fuzzy expert control. Med Phys; 31: 950 [abstract].

Lessard E, et al. 2006. Class solution for inversely planned permanent prostate implants to mimic an experienced dosimetrist. Med Phys; 33(8): 2773-82.

Nouranian S, et al. 2015. Automatic prostate brachytherapy preplanning using joint sparse analysis. MICCAI; 9350: 415-23.

O'Mara, D. et al. "Measuring bilateral symmetry in digital images." Proceedings of Digital Processing Applications (TENCON'96). vol. 1. IEEE, 1996.

Pokharel S, et al. 2013. Evaluation of hybrid inverse planning and optimization (HIPO) algorithm for optimization in real-time, high-dose-rate (HDR) brachytherapy for prostate. J Appl Clin Med Phys; 14(4): 4198.

Pouliot J, et al. 1996. Optimization of permanent 125I prostate implants using fast simulated annealing. Int J Radiat Oncol Biol Phys; 36(3): 711-20.

Xin X, et al. 2013. Spectral approximation to point set similarity metric. ICMEW/IEEE Proc: 1-4. Doi: 10.1109/ICMEW.2013.6618283.

* cited by examiner

KNOWLEDGE-BASED BRACHYTHERAPY PLANNING BASED ON PRIMITIVE FEATURES COMPUTED FROM ANATOMICAL CONTOUR DATA

CROSS-REFERENCE TO RELATED APPLICATIONS

This application represents the national stage entry of International Application PCT/CA2017/050150, filed Feb. 9, 2017, which claims the benefit of U.S. Provisional Application 62/293,878, filed Feb. 11, 2016. The contents of both applications are hereby incorporated by reference as set forth in their entirety herein.

BACKGROUND

The field of the present disclosure is systems and methods for radiation treatment planning. More particularly, the present disclosure relates to systems and methods for knowledge-based brachytherapy treatment planning.

Over sixty percent of all prostate cancers are diagnosed as localized disease. Low-dose rate ("LDR") brachytherapy—a form of internal radiation therapy—is one of the most effective methods for treating localized prostate cancer. Despite the significant benefits of LDR, utilization of the procedure among radiation oncologists has dropped in recent years. Publicity from poorly performed LDR cases, a high level of technical difficulty, and inadequate volumes of patients to train radiation oncologists on proper technique are suspected causes for this reduction.

Brachytherapy for localized prostate cancer typically involves the permanent implantation of 80-100 metallic seeds containing an x-ray-emitting radioisotope within the prostate gland using long, hollow needles. These seeds are implanted transperineally under transrectal ultrasound image-guidance in a pre-planned three-dimensional configuration. The seed configuration is designed manually, using computer software, by an expert radiation oncologist or medical physicist days-to-weeks before the actual implantation procedure. Manual planning is resource intensive, however, and requires expert skill that is established after executing several hundred treatments. Additionally, currently available automated treatment planning options cannot mimic plans that have been created by an expert planner.

Thus, there remains a need for systems and methods for brachytherapy planning that can automatically generate treatment plans having comparable quality to those manually generated by experienced practitioners. Preferably, these systems and methods will provide such automatically generated plans in clinically relevant time frames.

SUMMARY OF THE PRESENT DISCLOSURE

The present disclosure addresses the aforementioned drawbacks by providing a computer-implemented method for generating a brachytherapy plan. The method includes providing contour data for a patient to a computer system. The contour data indicates an anatomical contour for a target organ, which may be a prostate. A primitive feature is computed from the contour data, and a template brachytherapy plan is selected by querying a database using the primitive feature. The database contains stored contour data and stored brachytherapy plan configurations for different previously treated patients. A brachytherapy plan for the patient is then generated by performing, with the computer system, a stochastic search algorithm to adjust and further refine the selected template brachytherapy plan based on at least one clinical rule.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for knowledge-based brachytherapy planning. These systems and methods are capable of automatically generating treatment plans for prostate brachytherapy in clinically relevant times.

Case-based reasoning ("CBR"), a form of artificial intelligence mimicking human thought processes, is implemented here to solve many of the issues with automated brachytherapy planning methods. A CBR-based algorithm for guiding brachytherapy planning, termed knowledge-based brachytherapy ("KBBT") is described here. The systems and methods described here can significantly decrease the learning curve in brachytherapy planning and create clinically feasible plans in near real-time. Additionally, a decrease in staffing resources is expected to make brachytherapy more attractive to clinicians.

In general, the methods described here implement primitive features of anatomical contours to efficiently compare a particular patient's anatomy with plan configurations for different patients that are stored in a database. The "best-match" plan configuration in this database is used as a template to initialize a stochastic search for an optimal plan configuration for the particular patient.

Figure 1:
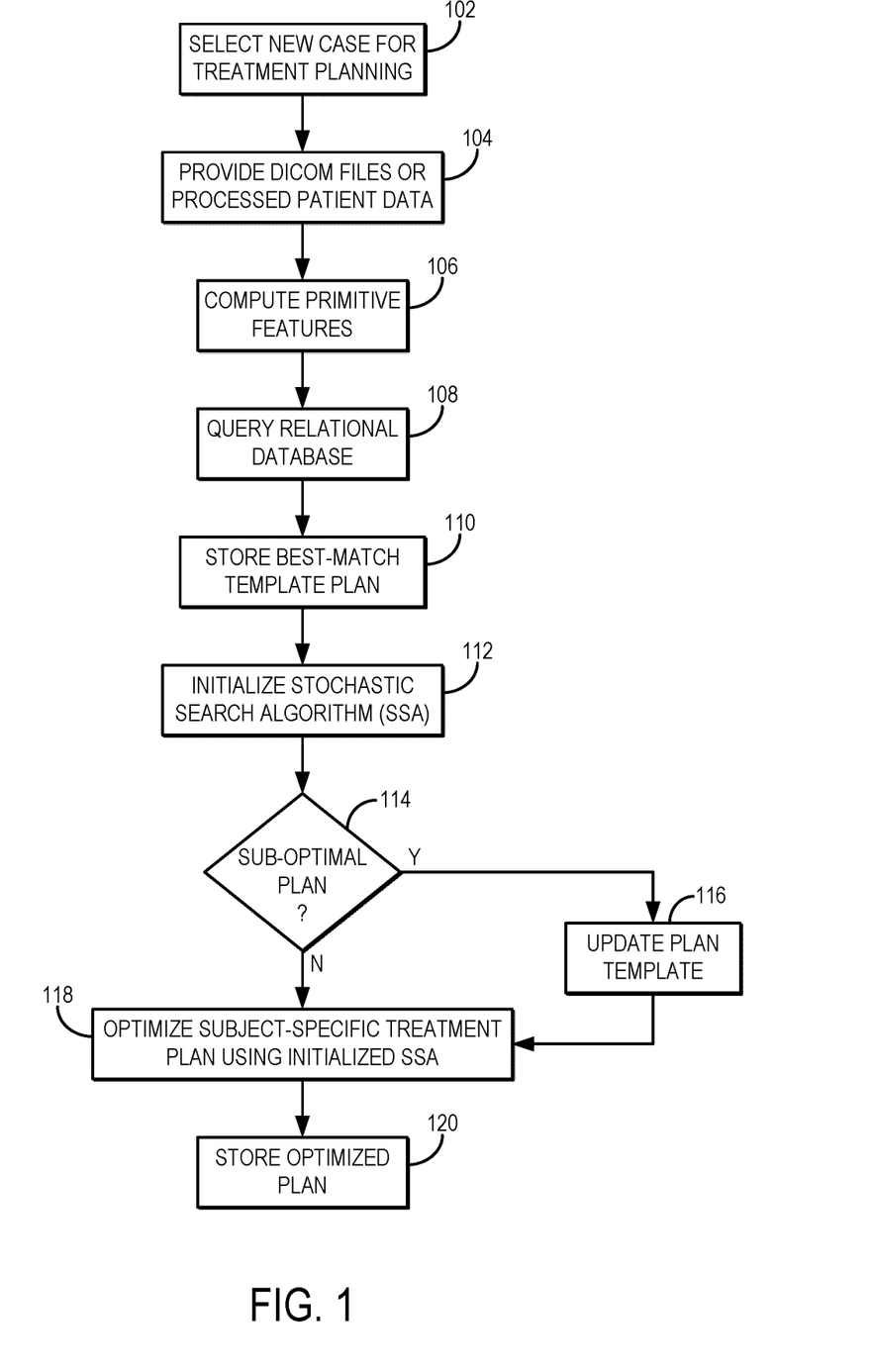
FIG. 1 is a flowchart setting forth the steps of an example method for generating a brachytherapy plan using a knowledge-based algorithm.

FIG. 1 illustrates a flowchart setting forth the steps of such an example algorithm for knowledge-based brachytherapy planning. In general, the method begins by selecting a new case that requires a treatment plan, as indicated at step 102. DICOM files, or other medical images and patient data, are then provided to a computer system, as indicated at step 104.

From the DICOM files, primitive features are computed, as indicated at step 106. In addition to these primitive features, additional information can be extracted from the DICOM files, including brachytherapist-defined contours (e.g., prostate, urethra, rectum, planning target volume ("PTV"), source and needle patterns, template placement, and radionuclide properties. This information can be extracted and stored in a training database together with the primitive features.

In general, primitive features provide a simplistic quantitative description of the subject's anatomy, and can be automatically extracted from prostate and organ-at-risk ("OAR") contour and coordinate data contained in the provided DICOM files. As will be described below, these primitive features provide speed, efficiency, and scaling that make the systems and methods described here highly effective at reducing dimensionality of data when large amounts of information are extracted from each prostate treatment space. Examples of primitive features include prostate volume, anterior-posterior ("AP") and left-right ("LR") profiles of the prostate, axial slice circumference, superior-inferior extent of the prostate, and symmetry around the mid-sagittal plane of the prostate. Examples for computing primitive features are provided below.

Figure 2A:
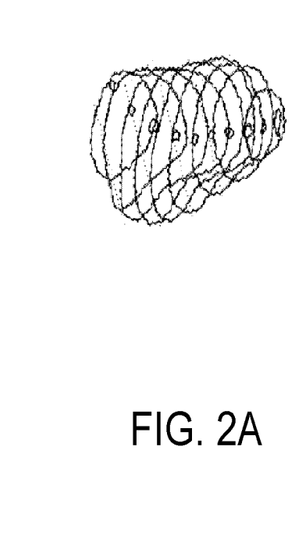
FIG. 2A is an example of three-dimensional contour data for a prostate.
Figure 2B:
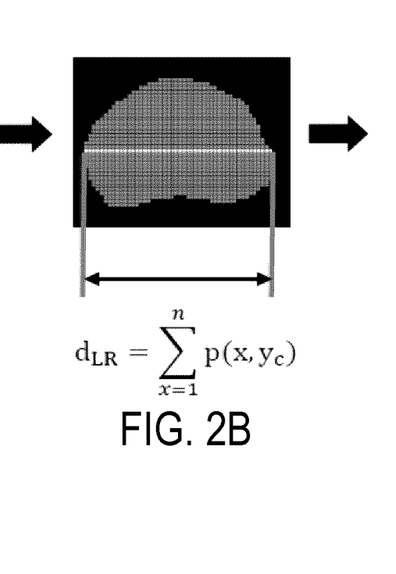
FIG. 2B is an example of a primitive feature, the left-right axis length, computed based on the contour data of FIG. 2A.
Figure 2C:
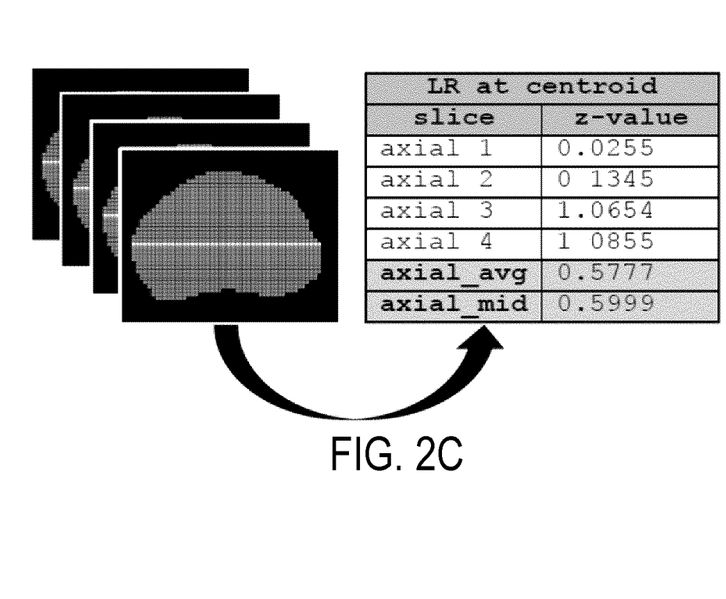
FIG. 2C is an example of left-right axis length data computed for a number of different axial slices based on the contour data of FIG. 2A.

As one example, one primitive feature that can be computed from the DICOM files includes features computed based on the length of the LR axis of the prostate. FIGS. 2A-2C illustrates an example process for computing primitive features based on, and including, the LR axis of the prostate. Three-dimensional contour data, an example of which is shown in FIG. 2A, is extracted from the provided DICOM files. A binary mask, an example of which is shown in FIG. 2B, is created from this contour data. The LR axis length can be measured at the y-axis centroid, $y_C$, of the prostate. The LR distance, $d_{LR}$, is computed as the sum of the binary pixel intensities with pixel values greater than one at the y-centroid across an axial prostate slice, as shown in FIG. 2B. These values are measured for each axial slice, as depicted in FIG. 2C. As mentioned above, additional features can be measured based on the length of the LR axis, including the mid-plane LR distance or the average across all slices. These values can be standardized prior to export.

Figure 3A:
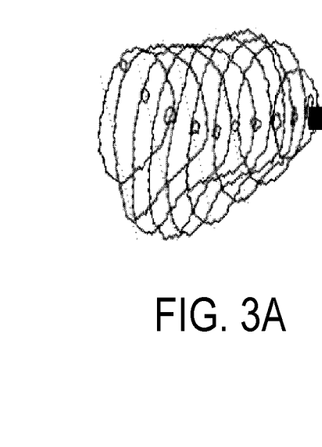
FIG. 3A is an example of three-dimensional contour data for a prostate.
Figure 3B:
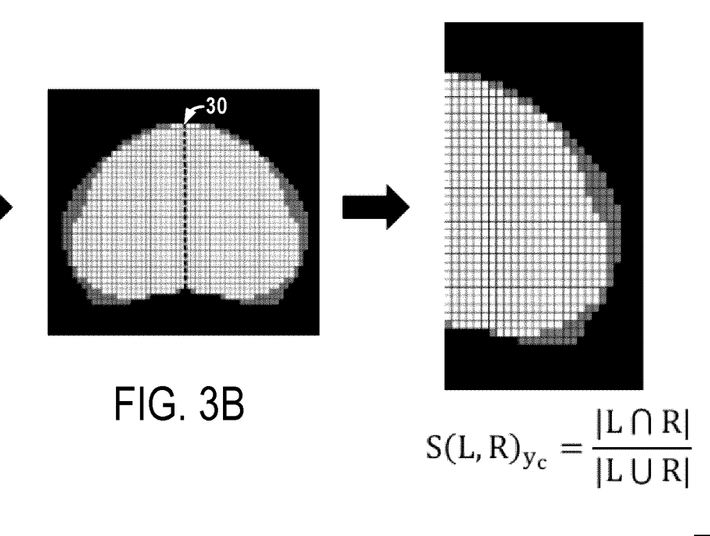
FIG. 3B is an example of an axial slice based on the contour data of FIG. 3A for which the left lobe of the prostate has been reflected onto the right lobe of the prostate.
Figure 3C:
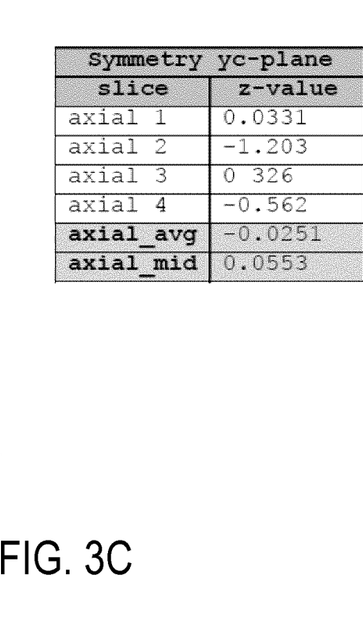
FIG. 3C is an example of a sagittal symmetry metric computed based on the contour data of FIG. 3A and the left-right lobe reflection of FIG. 3B.

As another example, one primitive feature that can be computed from the DICOM files includes a sagittal symmetry feature. Symmetry, in this case reflection symmetry, refers to the tendency for the prostate gland to be bilaterally symmetric around its sagittal plane. This characteristic defines not only a unique primitive feature of the prostate itself, but can also be used to guide the placement of brachytherapy needles and sources in a treatment plan. Similar to other primitive features, sagittal symmetry is computed by extracting a patient's prostate contour information, an example of which is shown in FIG. 3A. A binary mask is then created for each axial slice and the centroid of the prostate is then computed. The left-sided prostate lobe is reflected onto the right-sided lobe about the hyper-plane that passes through the y-axis centroid position, $y_C$, which is shown as the dashed line 30 in FIG. 3B. In FIGS. 3B and 3C, white pixel values represent areas of intersection between the left-side lobe and right-side lobe, while dark-grey areas represent non-symmetry in either left-side lobe or the right-side lobe.

The symmetry score, $S(L,R)_{y_C}$ about the y-centroid plane is the ratio of the intersection of the left (L) and right (R) lobes, to the union of the right and left lobes, $$S(L, R)_{y_c} = \frac{|L \cap R|}{|L \cup R|}. \tag{1}$$

This process is similar to computing a Jaccard Index, for each prostate lobe, about a hyper-plane. These values can be standardized prior to export. Symmetry values greater than zero represent increasingly symmetric bias towards the right lobe, symmetry values less than zero represent bias towards the left lobe, and zero-valued symmetry values represent symmetry between the left and right lobes.

Referring again to FIG. 1, after primitive features have been computed, a database containing a multitude of analytical information on prior successful prostate plans used in varying types of anatomical environments is queried, as indicated at step 108. In particular, the database is queried to identify one or more stored treatment plans with similar anatomical configurations as the new case. For instance, the query implemented at step 108 utilizes the primitive features computed in step 106 and compares them to primitive features stored in the database or primitive features computed or otherwise extracted from data contained in the database.

The database may be a non-relational database. As another example, the database can be a relational database ("RDB") that includes information obtained from multiple different subjects with lists of data being grouped into similar values by common keys, which can then be used to organize the information. Several of these connected databases constitute a data warehouse.

In one example configuration, the database can contain DICOM-RT files (e.g., RTPlan, RT Structure set, RTDose, and ultrasound images), from which prostate and organ-at-risk ("OAR") contour data, the plan configuration (i.e., the 3D position of radioactive sources within the prostate gland), and the dosimetric information of each radioactive source used can be extracted.

Figure 4:
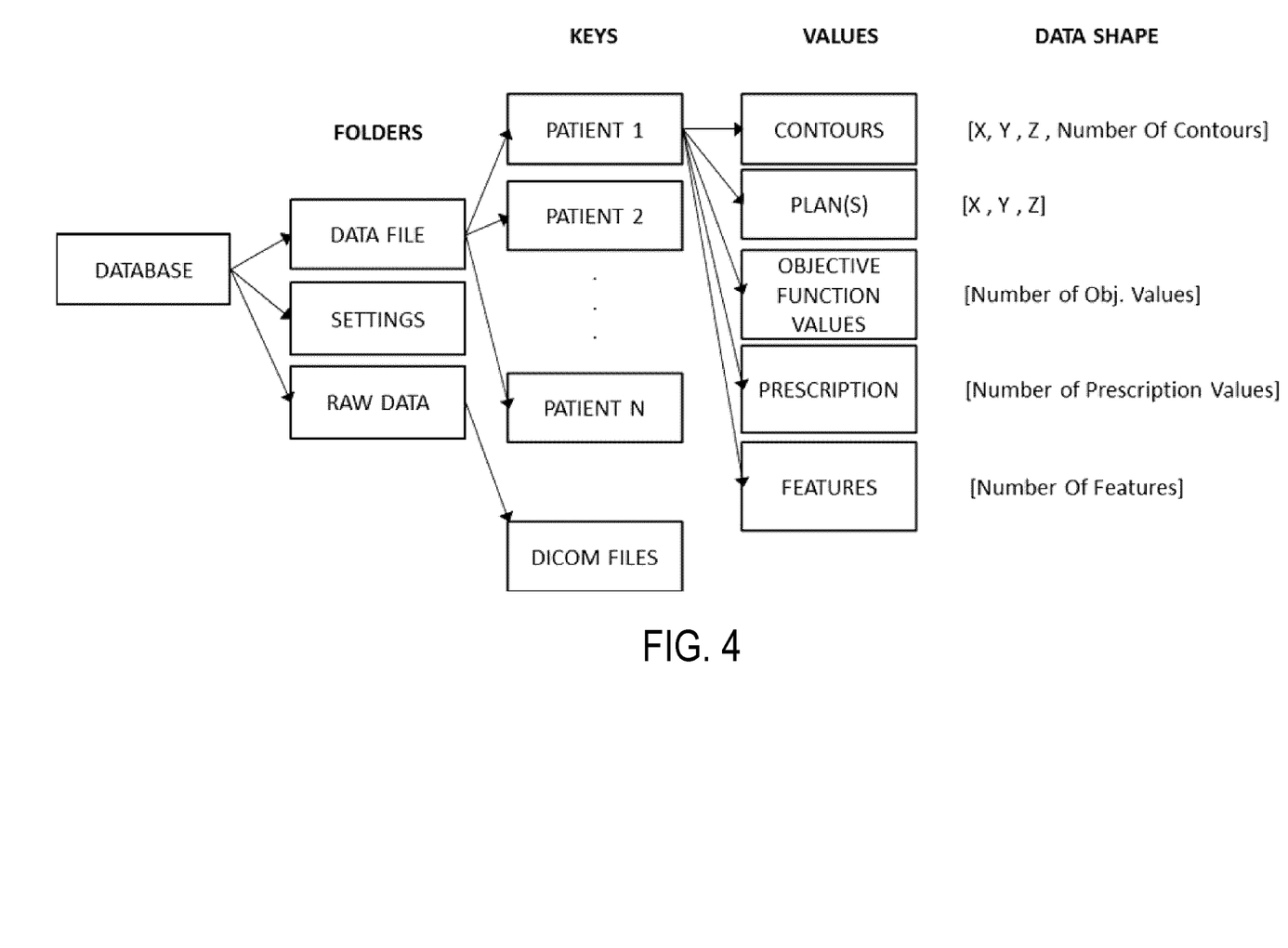
FIG. 4 is an example of a stratified structure of database files containing information about stored brachytherapy plan configurations.

FIG. 4 illustrates an example of a stratified structure of database files. In this example, the database includes "RAW DATA" that contains RTPlan, RTStruct, and RTDose files along with imaging files; a "SETTINGS" file that contains general settings and parameters for the algorithm; and a DATA file that contains data to be used in training or planning using the algorithm. The DATA file is primarily a non-relational database, but can also be a relational database, partitioned into "KEYS" that relate to a patient entry within the database and "VALUES" that may be any data format. For LDR planning, the VALUES can contain the contours, plans, stored objective function values during training, a set of prescription parameters, and primitive features for the patient entry. Data shapes define the structure of the data stored in the values and are typically multi-dimensional matrices.

Preferably, the treatment plans stored in the database include primitive features extracted from anatomical contours. As one example, these features can be computed and stored as z-score standardized values as well as summary files for quick-lookups. Additional data files can also be included as part of planning prescription and dosimetric computation files. The combination of the database with these data files constitutes a data warehouse, as mentioned above.

As one example, the treatment plans contained in the database can be low-dose rate ("LDR") plans. As a further example, each LDR plan can contain an ultrasound image volume with 9-12 axial images (e.g., 120 mm×120 mm×55 mm). The LDR plans can further include contours for the target organ (e.g., PTVs), OARs, and so on, that were contoured on the axial ultrasound images by a planning physician prior to treatment planning.

Referring again to FIG. 1, and as mentioned above, the database is queried at step 108 based on the primitive features computed in step 106 to find similarity between those same features within the database. The query operation thus serves as a classifier and retrieves the most similar plan configuration in the database to the new case that is likely to provide a semi-optimal planning solution.

As one example, the query operation can implement a multi-dimensional range-query algorithm to provide rapid computation. The range-query algorithm performs a "table look-up" within the database and retrieves plans with values matching those of the new case. In this example, the query is performed in a cascading format for all primitive features and is used to narrow down a list of plans matching anatomical features for the new case. The cascade pathway in this example is based on a decision tree carried out by expert brachytherapy planners.

Figure 5:
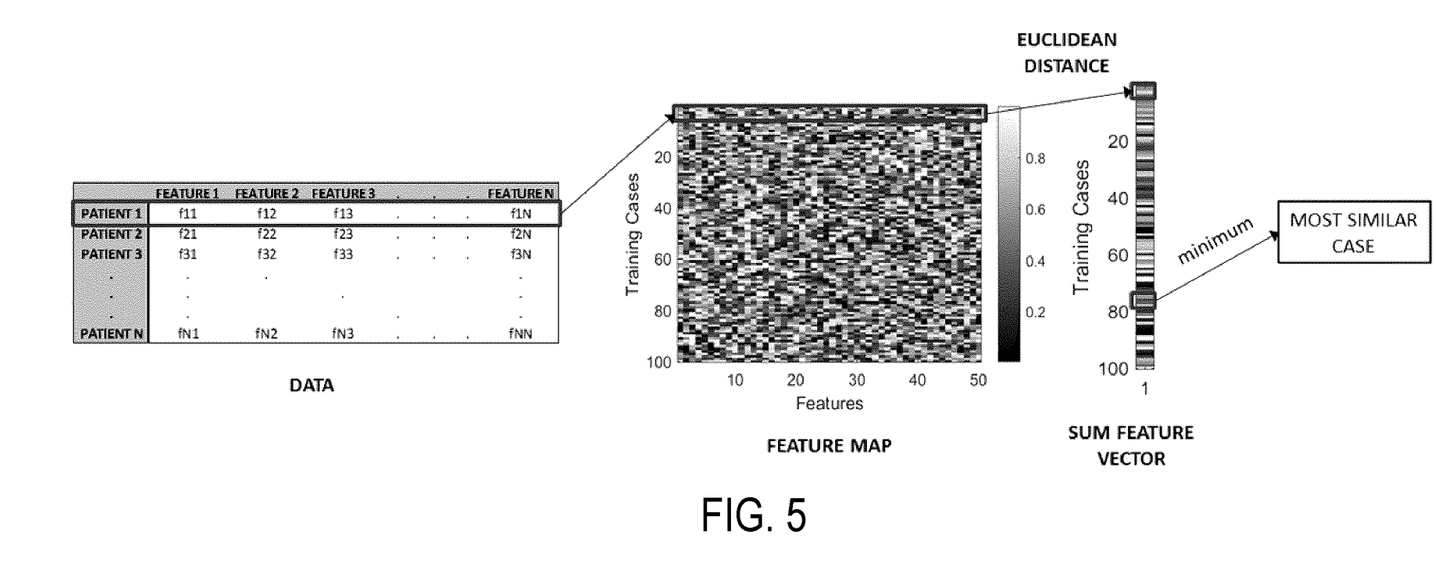
FIG. 5 depicts an example implementation of a range-query algorithm for querying a database based on primitive features computed from anatomical contour data.

FIG. 5 illustrates an example implementation of a range-query algorithm for finding the most similar plan in a database based on the primitive anatomical features. Data structured in the form of a table of values is shown for reference. In this example PATIENT1 is the query case associated with the most similar plan to this case. A feature map of the similarity between all features in the query case and those of all other database entries is produced. The feature map has the shape of the number of training cases (100 in this example), by the number of features (50 in this example). Lighter shaded values in the feature map are "more-similar" and darker shaded values in the feature map are "less-similar." To convert the feature map to a feature vector, the rows of the feature map are summed for all feature similarities using a Euclidean Distance metric. Finally, the smallest (or minimum) value(s) are used to select the most similar case to function as a starting template.

The similarity matching process finds the most similar features of cases from the training database that match those of the current case. As one example, a Euclidean distance metric can be used to inform a k-nearest neighbor ("kNN") plan retrieval. In this process, a vector representing the features for the query case can be given by, $$X=[x_1,\ldots,x_i]\in \mathbb{R}^1 \qquad (2);$$

where $x_1,\ldots,x_i$ represents the first to the $i^{th}$ computed anatomic feature. Similarly, a matrix representing the features for the database cases can be given by, $$Y=[y_{1,1},\ldots,y_{i,j}]\in \mathbb{R}^2 \qquad (3);$$

where $y_{1,1},\ldots,y_{i,j}$ represents identical features computed for the first to the $i^{th}$ feature for each $j^{th}$ database plan. To find the similarity vector, $\Pi=[\pi_1,\ldots,\pi_j]\in \mathbb{R}^1$, the following can be performed:

$$\forall j \in [0, M], \pi_j = \sqrt{\sum_{i=1}^{N}(x_i - y_{i,j})^2} \; ; \qquad (4)$$

where $\pi_1,\ldots,\pi_j$ represents the sum of the distance values for the $i^{th}$ feature, for all N features, between the query and database cases, respectively. Similarly, this can be computed for all M database cases to produce the similarity vector, $\Pi$. In this example, the kNN retrieval can then be used to retrieve the top k plans from the training database with the most similar anatomic features. The best matched plan or plans can then be populated onto the brachytherapist-defined contours prior to further optimization.

Referring again to FIG. 1, the output of the query process is storing the retrieved plan as a best-match template, as indicated at step 110. Once this template plan is selected, a stochastic search algorithm ("SSA") is used to adapt the template plan to the anatomy of the subject for which the new treatment plan is being generated. This process generally includes an initialization step and the SSA computation.

Thus, an SSA is initialized first, as indicated at step 112. In general, this initialization limits the iterative spaces that the SSA will search through and how the SSA can find a better solution. The initialization process converts the patient anatomy and the retrieved template plan from Cartesian coordinate points into sets of voxel indices in three-dimensional space. The search space for the SSA can also be defined using sets of clinical rules to determine where a plan is clinically allowed to place needles or radioactive source positions.

In some examples, clinical rules are used to limit potential source positions. For instance, anatomical contours, populated with a template plan and given a large search space of potential source positions, can limit these positions using several clinical rules. Clinical rules can be used in varying combinations to fine-tune the allowable changes in source positions to the template plan. A non-limiting list of example clinical rules is shown below in Table 1. This example list includes clinical rules corresponding to forbidding brachytherapy needles to be too close in proximity, and not allowing source positions to be outside the PTV margin, among others.

TABLE 1

Examples of clinical rules that can be applied to stochastic optimization. Low objective function values refer to values <5% of the initial objective function value.

| Type | Applied To | Rule | Range | Exception |
| --- | --- | --- | --- | --- |
| Never-Do | N | X | < Line 1 on template grid | None |
|  | N | A | Min. 1 axial prostate contour | None |

TABLE 1-continued

Examples of clinical rules that can be applied to stochastic optimization. Low objective function values refer to values <5% of the initial objective function value.

| Type | Applied To | Rule | Range | Exception |
|---|---|---|---|---|
| | N/S | X | ≤0.5 cm from N/S on axial plane | None |
| | S | X | = 1 per any needle | None |
| | N/S | X | >1.5 cm retraction from base plane | None |
| | N | X | c1, D1, d1 holes OR inf mid-line holes | Low objective: Allow D-line needle |
| Limits | N | Num | 36-40 | Prostate volume >60 cc |
| | S | Num | <100 | Prostate volume >60 cc |
| | N | Pos | >1 cm to urethral surface | Low objective: >0.5 cm allowed |
| | N | Pos | <0.5 cm to PTV OR in dilated PTV | Low objective: <0.8 cm isotropic OR posterior (to include seminal vesicles) |
| | S | Pos | 1 cm S-S spacing in needle | Low objective: apex + 1, base − 1 allow 0.5 cm spacing in needle |
| | N/S | Pos | Fully load apex/base planes with N/S | Within limits of applied rules |

Figure 6:
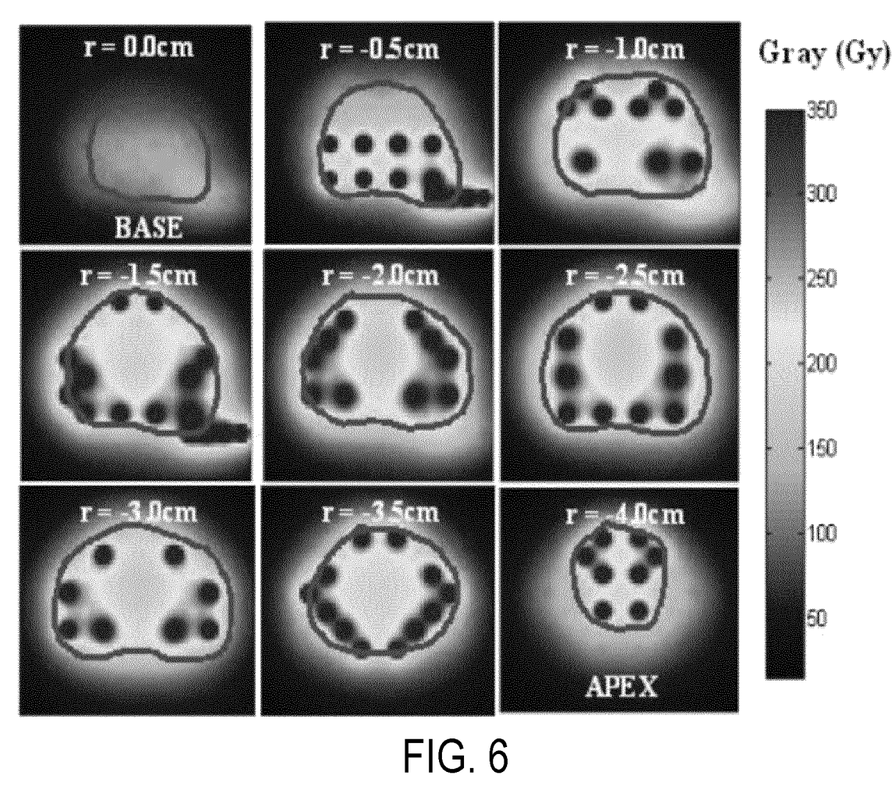
FIG. 6 is an example of consecutive axial slices of a three-dimensional isodose distribution modeled for a specified plan configuration showing the radiation dose delivered to the prostate gland, for which a prescription dose of 145 Gy was used.

Abbreviations:
N = Needle,
S = Source,
X = "Cannot Be",
A = "Always Must be",
Num = Number,
Pos = Position As part of the initialization process, a three-dimensional isodose distribution of the source configuration can be computed using a standardized dose formalism. An example of a modeled dose distribution for a generic source configuration is shown, along with the associated prostate contour, in FIG. 6.

Referring again to FIG. 1, in some embodiments, after the SSA is initialized, a determination is made at decision block 114 whether the template plan is sub-optimal, such as if there are areas of radiation dose in the target organ that do not meet the physician prescription. If the template plan is identified as being sub-optimal, such as if cold spots are identified, the template plan can be updated using various combinations of clinical rules to add seeds only to specific needles, as indicated at step 116.

After the SSA is initialized, the SSA is performed to adjust and optimize the template plan to the specific patient's anatomy, as indicated at step 118. The SSA uses the template plan to search potential plan configurations that satisfy target dose criteria. Examples of target dose criteria can involve physician-determined statistical criteria that a plan must meet in order to be implantable within a patient and deliver sufficient radiation dose. An example prescription dose criteria for the prostate and OARs are outlined in Table 2. The SSA will try to attain these values through varying source positions within the plan.

TABLE 2

Dose criteria for a typical permanent implant brachytherapy plan.

| Target/OAR | Criteria (% of prescription dose) | Acceptable Limits (% of prescription) |
|---|---|---|
| Prostate | V100% | >99% |
| | V150% | ≤60% |
| | V200% | ≤20% |
| | D90% | 113%-120% |

TABLE 2-continued

Dose criteria for a typical permanent implant brachytherapy plan.

| Target/OAR | Criteria (% of prescription dose) | Acceptable Limits (% of prescription) |
|---|---|---|
| PTV | V100% | >95% |
| Urethra | Dmax | <150% |
| Rectum | D1 cc | <100% |

V100% = Volume of the prostate contour receiving 100% of the prescription dose
D90% = Dose to 90% of the contour volume
cc = cubic centimeters Any suitable stochastic search algorithm can be implemented to search for an optimal source configuration that yields the desired target criteria. As one example, a simulated annealing ("SA") algorithm can be used. As another example, a single, linear objective function can be used together with a greedy descent algorithm. In some instances, the objective function can include aggregating multiple objective for different structures into a single objective function.

As one example, the best matched plan or plans obtained from the training database can be used to compute the dose to the contoured structure volumes. These doses can be computed using the TG43-U1 point-source formalism, or other suitable technique. The dose to each contoured structure can then be stored as a linearly-indexed vector, $$D = [d_1, \ldots, d_k] \in \mathbb{R}^3 \quad (5);$$

for the first to the $k^{th}$ voxel within or on the surface of the structure volume. Each voxel element of the structure that was not within a predefined dose range can be penalized. In one example, these voxels can be penalized according to, $$O(A) = \begin{cases} W \cdot |d_k - D_t| & \text{if } d_k < D_l \text{ or } d_k > D_h \\ 0 & \text{otherwise} \end{cases} ; \quad (6)$$

where $d_k$ is the $k^{th}$ voxel dose for a given structure volume, $D_t$ represents some pre-defined higher ($D_h$) and lower ($D_l$) dose limits of a structure, W is a weighting vector, and O(A) represents the objective function score for a given source pattern, A. The hyperparameters, $D_h$ and $D_l$, can be obtained by brachytherapist consultation and can, in some example, remain constant. The values of the weighting vector can be obtained using cross-validation on the initial training database.

Summing penalty scores for each voxel yields a cumulative objective function for a given structure. As one example, four objectives can be computed using Eqn. (6): one for prostate, one for PTV coverage, one for a uniformity constraint (i.e., representing a measure of dose heterogeneity for several sparse dose points within the prostate volume), and one for urethral maximum dose. In some other examples, an additional objective can be computed for a rectal dose constraint; however, if the initial quality of the plans found in the training database are high, it may be possible to remove this rectal dose constraint without significant dosimetric penalty. These objectives represent soft-constraints for the algorithm to achieve.

In addition to the soft-constraints provided by the dosimetric objective function, several clinical rules can be used as hard-constraints to limit attempted source patterns during stochastic optimization. Clinical rules can be designed through consultation with brachytherapist experts to identify source patterns that could lead to poor implantations. A list of example clinical rules is provided above in Table 1.

Figure 7:
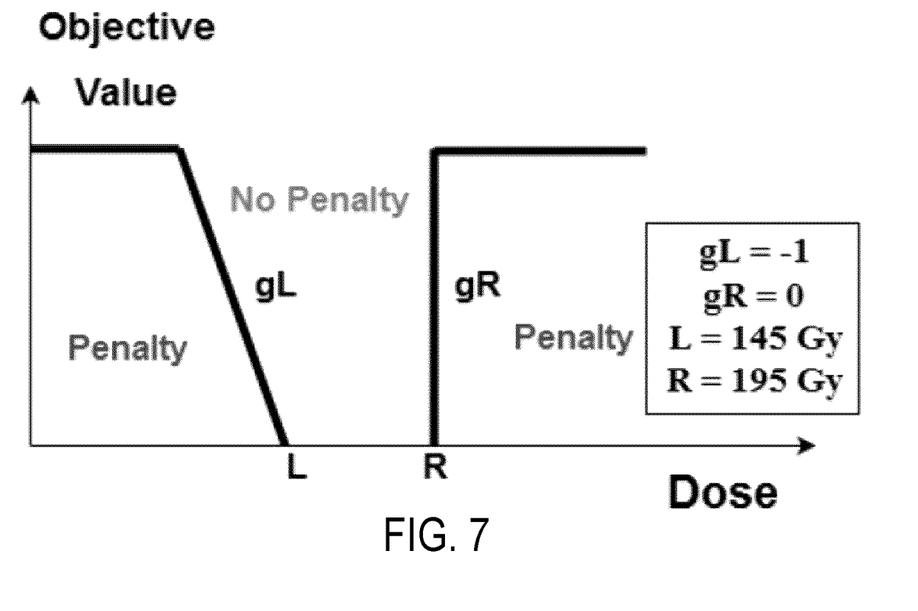
FIG. 7 is an example potential well that can be implemented in a stochastic search algorithm, such as a simulated annealing algorithm.

In example implementation using an SA algorithm, the search algorithm first requires input from a physician prescription, which can be stored in data files as part of the database. The prescription is pre-built, but can be altered for differing protocols, and defines the allowable ranges for the prostate and urethral doses. An example prescription is illustrated in FIG. 7, which shows the prescription as a potential-well, a graph of values used to add penalties to poorly performing plan configurations.

In this example, the prescription parameters are defined by a potential well. The x-axis in FIG. 7 shows the prostate dose and the y-axis shows the objective value (e.g., total penalty) for the organ. High penalty values create large objective values, and lower values represent smaller penalty values. The potential well indicates that the configuration organ dose is within the appropriate left (L) and Right (R) dose limits. The left and right gradients (gL and gR, respectively) represent the steepness of the objective value as a function of the dose.

The dose from each organ is compared to these prescription values and assigned a penalty weight if the plan configuration violates the given prescription doses. The aggregate of the penalty weights for all organs is called an objective function, O(i), for the $i^{th}$ state.

In the SA example, an initial temperature parameter is defined, along with a temperature reduction schedule. As the temperature drops (according to the scheduled reduction) the algorithm is less and less likely to accept plan configurations with objective gradients (i.e., the difference between consecutive objective functions), that are greater than zero (i.e., higher penalty states). Initially, as the algorithm starts local searches for new plan configurations, gradients slightly greater than zero will be allowed to "escape" the many local minima (or locally optimized plans, as opposed to globally optimized).

Figure 8:
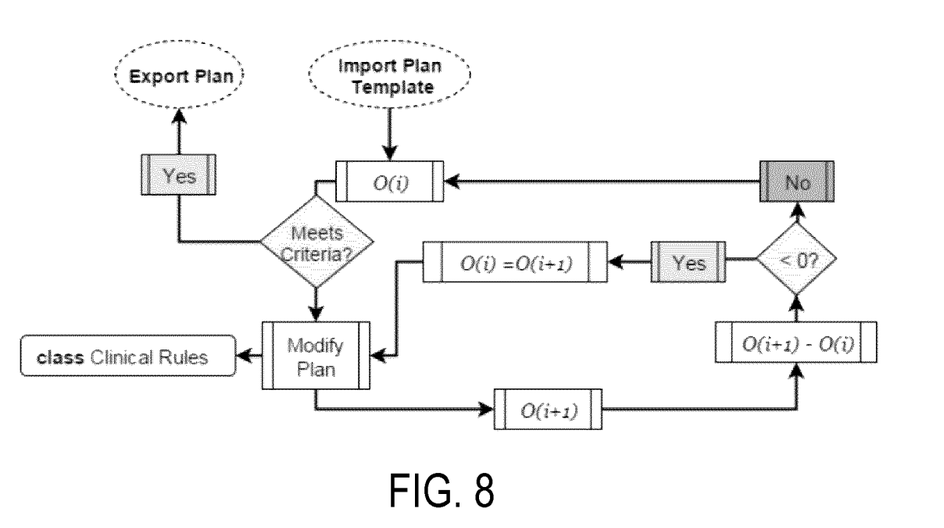
FIG. 8 is an example workflow diagram for a stochastic search algorithm implemented to adjust and update a template plan configuration retrieved from a database.

A procedural workflow of the example SSA algorithm is shown in FIG. 8. If a best possible solution is reached (adhering to both clinical rule and target dosimetric criteria), the solution is stored and the initial template is shifted in the anterior-posterior axis. This shifted template is then run again through the SSA loop. The secondary plan is then compared to the first plan, at which point the better of the two solutions (in terms of clinical rule adherence, dosimetric targets, and minimized objective function) is exported for physician evaluation. This finalized "plan competition" ensures as close to a clinically optimal plan is selected.

For instance, frequently evaluating clinical rules sources are added, deleted, or moved within the plan. Dosimetry for each new state, O(i+1), is computed and the difference between the old and new state, ΔO, is determined. If the difference between states is less than zero, the new configuration is kept. If the difference is not less than zero, the new configuration is accepted with some probability, or discarded. The new configuration is then assigned as the initial objective function for the next iteration, O(i). Once the best possible solution is found, the initial template is shifted and the SSA repeated. The final plan satisfies as many dosimetric and clinical criteria as possible. Plans are then exported to DICOM RT files.

The sagittal symmetry metric discussed above can be utilized not only in the selection of a best-match plan from the database, as described above, but can also be applied during the SSA step to maximize the sagittal symmetric quality of a finalized treatment plan.

Referring again to FIG. 1, once a finalized plan is generated by the SSA, the plan configuration is stored, as indicated at step 120. For instance, the plan configuration is written to a DICOM RT file and exported to the patient's brachytherapy planning folder within a specified server from which plan files can be retrieved by a brachytherapy planning station.

It will be appreciated by those skilled in the art that the treatment plans generated using the methods described above can be evaluated in a post-operative follow-up and, where the plans are deemed to be successful, the generated plan can be added to the database for use in instantiations of the treatment planning method for future patients.

Although the methods described above were described in relation to examples for generating LDR plans for brachytherapy of the prostate, it will be appreciated by those skilled in the art that the methods described here can also be implemented for other internal radiation treatment planning applications. As one example, the methods described here can be used for high-dose rate ("HDR") applications, including in prostate and gynecological applications. The methods described here can also be implemented for partial breast seed irradiation ("PBSI") applications.

Figure 9:
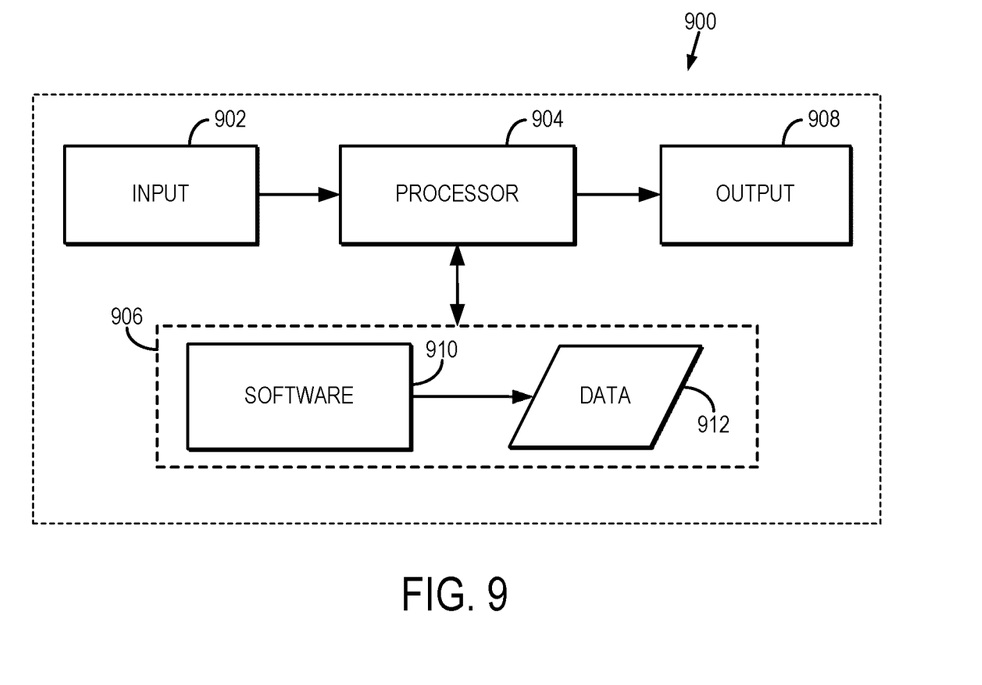
FIG. 9 is a block diagram of an example computer system that can implement the methods described here.

Referring now to FIG. 9, a block diagram is shown of an example computer system 900 for generating a brachytherapy plan, such as is described above in detail. The computer system 900 generally includes an input 902, at least one processor 904, a memory 906, and an output 908. The computer system 900 can also include any suitable device for reading computer-readable storage media. The computer system 900 may be, for example, a workstation, a notebook computer, a tablet device, a mobile device, a multimedia device, a network server, a mainframe, or any other general-purpose or application-specific computing device. The computer system 900 may operate autonomously or semi-autonomously, or may read executable software instructions from the memory 906 or a computer-readable medium (e.g., a hard drive, a CD-ROM, flash memory), or may receive instructions via the input 902 from a user, or any another source logically connected to a computer or device, such as another networked computer or server. In general, the computer system 900 is programmed or otherwise configured to implement the methods and algorithms described above.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as DICOM files, contour data, primitive feature data, or associated data. As described above, this data can be retrieved from a database, such as a non-relational database or a relational database ("RDB"), that is in communication with the computer system 900. Such data may be processed as described above. In addition, the input 902 may also be configured to receive any other data or information considered useful for generating a brachytherapy plan according to the methods described here.

Among the processing tasks for operating the computer system 900, the at least one processor 904 may also be configured to receive data, such as DICOM files, contour data, primitive feature data, or associated data. In some configurations, the at least one processor 904 may also be configured to carry out any number of post-processing steps on data received by way of the input 902. In addition, the at least one processor 904 may be capable of computing primitive features, initializing a stochastic search algorithm, and implementing a stochastic search algorithm, as described above.

The memory 906 may contain software 910 and data 912, and may be configured for storage and retrieval of processed information, instructions, and data to be processed by the at least one processor 904. In some aspects, the software 910 may contain instructions directed to generating brachytherapy plans as described above. Also, the data 912 may include any data necessary for operating the computer system 900.

In addition, the output 908 may take any shape or form, as desired, and may be configured for displaying, in addition to other desired information, brachytherapy plans or reports generated based on the generated brachytherapy plans.

The present disclosure has described one or more preferred embodiments, and it should be appreciated that many equivalents, alternatives, variations, and modifications, aside from those expressly stated, are possible and within the scope of the invention.

The invention claimed is:

1. A computer-implemented method for generating a brachytherapy plan, the steps of the method comprising:
   (a) providing contour data for a patient to a computer system, the contour data indicating an anatomical contour for a target organ;
   (b) computing with the computer system, a primitive feature from the contour data;
   (c) selecting a template brachytherapy plan by querying a database using the primitive feature, the database containing stored contour data and stored brachytherapy plan configurations for different previously treated patients; and
   (d) generating a brachytherapy plan for the patient by performing with the computer system, a stochastic search algorithm to adjust the selected template brachytherapy plan based on at least one clinical rule.

2. The method as recited in claim 1, wherein the primitive feature is a symmetry value that indicates a symmetry of the target organ in an anatomical plane.

3. The method as recited in claim 2, wherein the target organ is a prostate and the anatomical plane is a sagittal plane.

4. The method as recited in claim 3, wherein the symmetry value is computed by generating a binary mask of the prostate from the contour data, dividing the binary mask into a left lobe area and a right lobe area, and computing the symmetry value as a ratio of an intersection of the left lobe area and the right lobe area to a union of the left lobe area and the right lobe area.

5. The method as recited in claim 4, wherein dividing the binary mask include calculating a centroid of the binary mask and dividing the binary mask based on the centroid.

6. The method as recited in claim 1, wherein step (c) includes selecting the template brachytherapy plan based on a comparison of the primitive feature to primitive features extracted from the stored contour data.

7. The method as recited in claim 6, wherein the database is queried using a multi-dimensional range-query algorithm.

8. The method as recited in claim 7, wherein the range-query algorithm implements a hierarchy of primitive features to select the template brachytherapy plan from the database.

9. The method as recited in claim 8, wherein the range-query algorithm is performed in a cascading format for the hierarchy of primitive features, wherein the cascading format implements a cascading pathway based on a decision tree.

10. The method as recited in claim 1, wherein step (d) includes adjusting the template brachytherapy plan based on the primitive feature.

11. The method as recited in claim 10, wherein the primitive feature is a symmetry value that indicates a symmetry of the target organ in an anatomical plane, and adjusting the template brachytherapy plan based on the primitive feature includes maximizing the symmetry value.

12. The method as recited in claim 1, wherein step (d) includes initializing the stochastic search algorithm based on the selected brachytherapy plan template to define a restricted search space for the stochastic search algorithm.

13. The method as recited in claim 1, wherein step (d) includes identifying dosimetric cold spots in the template brachytherapy plan and updating the template brachytherapy plan using the at least one clinical rule to determine where additional seeds should be added in the template brachytherapy plan.

14. The method as recited in claim 1, wherein the contour data provided in step (a) also indicates an anatomical contour for at least one organ-at-risk (OAR).

15. The method as recited in claim 1, wherein the contour data provided in step (a) comprises a series of two-dimensional contours that collectively indicate a three-dimensional contour.

16. The method as recited in claim 15, wherein each contour in the series of two-dimensional contours is a contour in an axial plane through the target organ.

17. A computer-implemented method for generating a symmetry metric from anatomical contour data computed from medical images that depict a subject, the steps of the method comprising:
   (a) providing the anatomical contour data to a computer system, the anatomical contour data indicating an anatomical contour for a target organ in the subject;
   (b) computing with the computer system, a binary mask of the target organ using the anatomical contour data;

(c) computing with the computer system, an axis of reflection for the target organ, the axis of reflection defining an axis about which symmetry of the target organ will be measured;

(d) computing with the computer system based on the binary mask, a symmetry metric that provides a quantitative value indicating symmetry of the target organ about the axis of reflection; and (e) generating a report based on the computed symmetry metric.

18. The method as recited in claim 17, wherein step (d) includes dividing the binary mask into a first area and a second area using the axis of reflection, and computing the symmetry metric as a ratio of an intersection of the first area and the second area to a union of the first area and the second area.

19. The method as recited in claim 18, wherein the target organ is a prostate, the first area indicates an area of a left lobe of the prostate in a sagittal plane, and the second area indicates an area of a right lobe of the prostate in the sagittal plane.

* * * * *